United States Patent [19]

Sakai et al.

[11] Patent Number: 4,938,964
[45] Date of Patent: Jul. 3, 1990

[54] EXTERNAL DERMATOLOGICAL COMPOSITION

[75] Inventors: Yasuyuki Sakai, Tokyo; Toyoaki Ishikura; Kazuo Kanbayashi, both of Yokohama; Tadashi Kato; Koichi Abe, both of Tatsuno, all of Japan

[73] Assignee: Showa Denko Kabushiki Kaisha, Tokyo, Japan

[21] Appl. No.: 281,356

[22] Filed: Dec. 8, 1988

[30] Foreign Application Priority Data

Dec. 9, 1987 [JP] Japan .................. 62-312675

[51] Int. Cl.$^5$ .............................................. A01R 9/70
[52] U.S. Cl. .................................... 424/443; 424/448; 424/449; 424/81
[58] Field of Search ............... 424/448, 449, 443, 444, 424/81

[56] References Cited

U.S. PATENT DOCUMENTS

| | | | |
|---|---|---|---|
| 4,740,374 | 4/1988 | Nakano et al. | 424/449 |
| 4,765,974 | 8/1988 | Tokuda et al. | 424/448 |
| 4,772,470 | 9/1988 | Inoue et al. | 424/81 |

FOREIGN PATENT DOCUMENTS

| | | |
|---|---|---|
| 0225005 | 6/1987 | European Pat. Off. . |
| 0289627 | 11/1988 | European Pat. Off. . |
| 57-81409 | 5/1982 | Japan . |
| 58-29706 | 2/1983 | Japan . |
| 58-38212 | 3/1983 | Japan . |
| 58-39616 | 3/1983 | Japan . |
| 58-103311 | 6/1983 | Japan . |
| 59-84817 | 5/1984 | Japan . |
| 59-172418 | 9/1984 | Japan . |
| 60-5569 | 2/1985 | Japan . |
| 60-185713 | 9/1985 | Japan . |
| 60-59207 | 12/1985 | Japan . |
| 61-148117 | 7/1986 | Japan . |
| 61-275212 | 12/1986 | Japan . |
| 62-273913 | 11/1987 | Japan . |

OTHER PUBLICATIONS

Patent Abstracts of Japan, vol. 10, No. 128 (C-345)[2185], May 13, 1986, JPA-60252412, Nichiban K.K.
Life Sciences, vol. 39, No. 12 (1986) pp. 1043-1050.
Therapeutic Research, vol. 3, No. 6 (1985) pp. 1099-1116.

*Primary Examiner*—Thurman K. Page
*Assistant Examiner*—Leon R. Horne
*Attorney, Agent, or Firm*—Sughrue, Mion, Zinn, Macpeak & Seas

[57] ABSTRACT

An external dermatological composition containing a drug supply layer carried on a support and containing 5% to 35% by weight of ketoprofen in an acrylic or methacrylic copolymer, which copolymer is composed of (i) 0.5% to 11.0% by weight of an $\alpha,\beta$-unsaturated carboxylic acid or its anhydride, (ii) 0.1% to 28.0% by weight of a vinyl monomer, (iii) 1.0% to 5.5% by weight of a hydroxy $C_2$-$C_4$ alkyl ester of acrylic or methacrylic acid, and (iv) a balance of a $C_4$-$C_{18}$ alkyl ester of acrylic or methacrylic acid, and has a glass transition point of $-15°$ C. to $-70°$C.

9 Claims, No Drawings

EXTERNAL DERMATOLOGICAL COMPOSITION

BACKGROUND OF THE INVENTION

1. Field of the Invention

The present invention relates to an external dermatological composition containing an anti-inflammatory drug ketoprofen. More specifically, it relates to an external dermatological composition having a remarkably enhanced percutaneous absorption realized by incorporating ketoprofen in a specific (meth)acrylic copolymer.

2. Description of the Related Art

Ketoprofen (3-Benzoylhydratropic acid), a non-steroidal anti-inflammatory drug, was developed in 1967, and is useful for the treatment of rheumatoid arthritis, osteoarthrosis, low back pains, neuralgia, trauma, postoperation, acute upper respiratory tract infection, and is widely used in peroral capsules, suppositories, and intramuscular injection agents.

Generally, however, the capsules, suppositories, and intramuscular agents containing this drug have a relatively short acting time of only 4 to 6 hours, and it is reported that problems arise such as an insufficient effect at a topical afflicted site having pain or gastroenteric disorders, or rarely, side effects such as low body temperature shock. Furthermore, it is believed that these problems arising from the use of capsules, suppositories, and intramuscular agents can be effectively solved by a percutaneous absorption of the drugs (see Ther. Res. 3(6), 1099 (1985)).

In addition, it is reported that a percutaneous absorption of drugs has an intimate correlationship with liposolubility and the percutaneous absorption of a series of non-steroid type anti-inflammatory drugs shows a parabolic correlationship with a partition coefficient rate of a drug between water and octanol. Ketoprofen in particular has a good partition balance between water and octanol (i.e., good hydrophilicity and lipophilicity balance and high percutaneous absorption (see Life Science, 39(12), 1043 (1986)).

In view of the above background, to enable the excellent antiflammatory activity possessed by ketoprofen to be exhibited topically, and at the same time to alleviate systemic side effects, ointments and poultices were recently developed and employed for the therapy of acute diseases having relatively light symptoms, such as tendovagnitis, peritendinitis, epicondylitis lateral, and myalagia, and for an improvement of the therapeutical effect of chronic diseases by using a combination of capsules and suppositories.

To enable such a topical percutaneous absorptive agent to exhibit the desired treatment effect, the problem is how to migrate the drug effectively from the preparations into the skin, and further into the subcutaneous muscle, synovia, or synovial membrane located under the skin. As far as the present inventor are aware, in currently available commercial ointments and poultices, the drug absorption through the skin is low: For example, the excreted ratios in urine, usually taken as an index of absorption, are 2.1% of the dosage in the case of ointments and 4.7% of the dosage in the case of poultices, which are about 1/35 to 1/15 compared with the 70% of those of the capsules or suppositories.

Furthermore, concerning the drug concentration in blood, the $C_{max}$ of ointments is 150 ng/ml in the case of a 300 mg dosage and the $C_{max}$ of poultices is 43 ng/ml in the case of a 30 mg dosage, which are remarkably low when compared with the $C_{max}$ of 6000 ng/ml of capsules (dosage=75 mg).

On the other hand, widespread studies have been made of percutaneous absorption promoting substances, which are intended to enhance the drug diffusibility through the skin by using a chemical substance.

According to the knowledges of the present invention, as attempts to enhance the percutaneous absorption of ketoprofen in ointments, and poultices, there have been proposed a method in which a solution thereof dissolved in peppermint oil is formulated in an ointment (Japanese Unexamined Patent Publication (Kokai) No. 58-29706), a method in which ketoprofen is formulated in an ointment together with fatty acid esters, waxes, surfactants, and hydrocarbons (Japanese Unexamined Patent Publication (Kokai) No. 58-39616), and a method in which ketoprofen is formulated in an ointment together with higher alcohols, hydrocarbons, and emulsifiers (Japanese Unexamined Patent Publication (Kokai) No. 58-103311), etc.

According to these methods, however, the drug migration ratio to the skin is only 14 to 20% of the drug dosage, and a satisfactory absorption thereof cannot be obtained.

Also, proposals have been made for a poultice containing a basic amino acid formulated therein (Japanese Unexamined Patent Publication (Kokai) No. 57-81409) and a poultice having an emulsifier and a dissolving aid added therein (Japanese Unexamined Patent Publication (Kokai) No. 61-275212), but these provide only a 2-fold enhancement of the drug absorption compared to that where there is no addition, and thus do not give a satisfactory effect.

Accordingly, the percutaneous absorption of ketoprofen is low for ointments and poultices, and thus a satisfactory therapeutical effect on a disease in a portion deep beneath the skin cannot be obtained, and further, substantially no effect on systemic diseases is exhibited.

On the other hand, a tape agent comprising a pressure sensitive adhesive composed mainly of a (meth)acrylic copolymer laminated on a plastic film support is thought to be an effective means of enhancing the percutaneous absorption of a drug, for the reasons given below, and studies have been made of this subject with regard to a large number of drugs, including ketoprofen:

(1) nonionic type molecular species, which migrate into skin better than ionic type molecular species, have a higher solubility in a tape than in ointments and poultices;

(2) since the base (adhesive layer) thickness is only about 10 μm, the diffusion distance for the drug is shorter than in poultices;

(3) the tape has a occlusive effect obtained through the support and the tackifier layer;

(4) since the tape is flexible and has a stronger adhesive power than poultices, it can be used for plastering at a curved site which is subjected to a large amount of movement, such as a joint;

To enhance the percutaneous absorption of the (meth)acrylic adhesive tape agent, the following points must be observed:

(1) an adhesive base must be used in which the drug is highly soluble and diffusibile;

(2) a nonionic drug must be formulated in as high a concentration as possible; and (3) the base thickness must be as thin as possible while maintaining a sufficient adhesion to the skin.

Further, with regard to the adhesive, the following requirements must be met:

(4) it must be chemically inert to the drug;

(5) there must be no change with a lapse of time of the drug releasability and adhesion to the skin; and (6) it must have a low irritation of the skin.

As a method for enhancing the drug concentration in the base, there have been proposed:

(i) a method in which an adhesive layer containing a drug at a saturated solubility or higher is laminated on a support to which the drug can migrate (Japanese Patent Publication (Kokoku) No. 60-59207;

(ii) a method in which the surface layer of a support to which the drug can migrate is crosslinked, and an adhesive layer containing a drug at a saturated solubility or higher is laminated thereon (Japanese Unexamined Patent Publication (Kokai) No. 59-172418);

(iii) a method in which a drug is contained at a saturated solubility or higher in an adhesive layer, and the drug in the supersaturated portion is uniformly dispersed therein in the form of fine particles (Japanese Unexamined Patent Publication (Kokai) No. 60-185713);

(iv) a method in which a drug is contained at a saturated solubility or higher in an adhesive layer in which fine particles of an acrylic polymer are dispersed (Japanese Unexamined Patent Publication (Kokai) No. 61-148117); and, (v) a method in which a drug solution in a good solvent for that drug is added to an adhesive solution in a poor solvent for that drug, to prepare a dispersion of fine particles of the drug, and the layer containing same is laminated on a support (Japanese Unexamined Patent Publication (Kokai) No. 62-273913); etc.

According to these methods, however, fine crystals of the drug dispersed in the adhesive layer will grow during storage, and thus problems arise such as a loss of drug releasability or a lowered adhesion to the skin.

To make the base layer thinner, the following methods have been proposed:

(i) a method in which an adhesive layer not containing the drug is provided on a support, and an adhesive layer containing the drug is applied thereover (Japanese Examined Patent Publication (Kokoku) No. 60-5569);

(ii) a method in which a drug is coated on the surface by which the adhesive layer is adhered to the skin, uniformly and sparsely over a predetermined area (Japanese Unexamined Patent Publication (Kokai) No. 58-38212);

(iii) a method in which adhesive layers having different drug contents are laminated on a support (Japanese Unexamined Patent Publication (Kokai) No. 59-84817); and (iv) a method in which an adhesive is coated on a support, and then a drug is coated thereon (Japanese Unexamined Patent Publication (Kokai) Nos. 55-160716, 55-164623, 59-227820).

According to these methods, in the production of the tape preparations, drugs exist in a limited portion of the surface or near the surface of the adhesive layer, but are naturally diffused throughout the whole adhesive layer during storage, and thus the problem of a lowered absorption arise.

As a method of enhancing the absorption of ketoprofen by using an additive substance, there have been proposed a method in which a keratin soluble enzyme (Japanese Unexamined Patent Publication (Kokai) No. 61-28231, a N-acylsarcosine (Japanese Unexamined Patent Publication (Kokai) No. 62-96430), an aliphatic monoalkylolamide (Japanese Unexamined Patent Publication (Kokai) No. 62-103015), or an organic acid (Japanese Unexamined Patent Publication (Kokai) No. 62-126119), is added.

Nevertheless, although examples of the subject drugs are given in the specification, there is no explanation of the absorption of ketoprofen, and the effect thereof is only to provide a 2-fold enhancement of the absorption of an antiinflammatory drug having a similar effect (e.g., indomethacin and fenoprofen), or a 10 to 15% enhancement of the drug skin migration ratio.

Further, to enhance the drug releasability from the adhesive layer and promote the percutaneous absorption, methods have been disclosed in which glycols such as polyethylene glycols, hydrocarbons such as fluid paraffins, and phthalic acid type plasticizers are added (see Japanese Patent Publication (Kokoku) Nos. 58-23366, 59-6285, 61-59607 and Japanese Unexamined Patent Publication (Kokai) Nos. 57-7413, 59-175418, 60-123417, 62-230715). But these additives not only exhibit no effect unless added in large amounts, but also exhibit a plasticizing effect of the adhesive, resulting in a lowering of the adhesive force.

Therefore, although ketoprofen has an excellent antiinflammatory activity, a technique for permitting the amount of drug necessary for exhibiting a higher topical action or systemic action to be effectively percutaneously absorbed through the skin has not been established.

The absorption of a drug is most affected by the physical properties of the adhesive as the drug supply layer, and it is important to find an adhesive having an excellent solubility, diffusibility, and partition coefficient to the skin, of a drug.

Here, the solubility, diffusibility, and partition coefficient to the skin of a drug are properties antagonistic to each other. For example, in a base with a low solubility of a drug, the diffusibility ($D_v$) and partition coefficient to the skin ($K$) become higher, but the drug concentration ($C_v$) is lowered. Conversely, in a base with a high solubility of a drug, the $C_v$ becomes higher but the $D_v$ and $K$ are lowered.

Therefore, an adhesive having a good balance between the $C_v$ and $D_v$ and $K$, which balance depends on the physical properties of the subject drug (e.g., molecular structure, electrostatic potential, lipid solubility melting point and others, must be selected), and each drug must be individually examined (see "Development Manual of Percutaneously Applied Preparations (1985)").

As conventional (meth)acrylic acopolymers proposed as the adhesive for tape agent, known to the present inventors, there have been proposed:

(i) copolymers of alkyl acrylates having $C_4$ or higher alkyl groups and acrylic acid (Japanese Patent Publication (Kokoku) No. 52-31405);

(ii) copolymers of alkyl acrylates having $C_4$ or higher alkyl groups, vinyl acetate or methyl methacrylate, and (meth)acrylic acid and polyfunctional compounds containing 2 or more double bonds in one molecule (Japanese Patent Publication (Kokoku) No. 59-3965); and (iii) copolymers of alkyl (meth)acrylates having $C_{4-12}$ alkyl groups, at least one monomer selected from the group consisting of alkyl (meth)acrylates having $C_{1-3}$ alkyl groups, vinyl acetate and styrene, and $\alpha,\beta$-unsaturated carboxylic acids (Japanese Unexamined Patent Publication (Kokai) No. 60-252412).

The solubility of ketoprofen in these adhesives, however, is limited to about 5% by weight, and thus a problem arises of a low percutaneous absorption.

On the other hand, to enhance the solubility of a drug in the adhesive, (meth)acrylic copolymers comprising polar monomers as mentioned below have been proposed as the component to be copolymerized:

(i) a (meth)acrylate having an ether group in molecule (Japanese Patent Publication (Kokoku) Nos. 58-23846, 59-7687, 59-7689, 61-26967, Japanese Unexamined Patent Publication (Kokai) No. 62-77316);

(ii) a vinyl alkyl ether (Japanese Patent Publication (Kokoku) Nos. 61-59607, 62-21395);

(iii) a vinyl compound having an amide bond in molecule (Japanese Unexamined Patent Publication (Kokai) Nos. 59-181214, 60-161917);

(iv) a (meth)acrylamide derivative having an amino group (Japanese Unexamined Patent Publication (Kokai) No. 62-228008); and (v) a (meth)acrylate of polyoxyalkylene glycol (Japanese Unexamined Patent Publication (Kokai) No. 61-33114).

The adhesives containing these monomers have an excellent ketoprofen solubility, and crystals are not precipitated when the drug is formulated in an amount of about 40% by weight. Nevertheless, because the ketoprofen solubility is very high, the drug migration to the skin is as low as 15 to 20%, and thus a satisfactory absorption cannot be obtained.

Therefore, the problem to be solved by the present invention is to find a (meth)acrylic copolymer having the best ketoprofen solubility, diffusibility, and partition coefficient to the skin.

SUMMARY OF THE INVENTION

Accordingly, the objects of the present invention are to eliminate the above-mentioned problems of the prior art and to provide an external dermatological composition having a remarkably enhanced percutaneous absorption.

Other objects and advantages of the present invention will be apparent from the following description.

In accordance with the present invention, there is provided an external dermatological composition comprising a drug supply layer carried on a support and containing 5% to 35% by weight of ketoprofen in an acrylic or methacrylic copolymer, which copolymer comprises (i) 0.5% to 11.0% by weight of an $\alpha,\beta$-unsaturated carboxylic avoid or an anhydride thereof, (ii) 0.1% to 28.0% by weight of a vinyl monomer, (iii) 1.0% to 5.5% by weight of a hydroxy $C_2$–$C_4$ alkyl ester of acrylic or methacrylic acid, and (iv) a balance of a $C_4$–$C_{18}$ alkyl ester of acrylic or methacrylic acid, and has a glass transition point of $-15°$ C. to $-70°$ C.

DESCRIPTION OF THE PREFERRED EMBODIMENTS

The constitution of the present invention is described in more detail as follows.

The $\alpha,\beta$-unsaturated carboxylic acid or the anhydrides thereof usable as the component (i) of the (meth)acrylic copolymer according to the present invention may include, for example, acrylic acid, methacrylic acid, crotonic acid, itaconic acid, maleic acid, fumaric acid, and maleic anhydride. Particularly, acrylic acid and maleic anhydride are preferably used.

Further, examples of the vinyl monomer usable as the component (ii) of the present invention are vinyl acetate, vinyl propionate, acrylonitrile, styrene, vinyl versatate, vinyl chloride, and the like. Particularly, vinyl acetate is preferably used.

The hydroxy $C_2$–$C_4$ alkyl (meth)acrylate usable as the component (iii) of the present invention may include 2-hydroxyethyl acrylate, 2-hyiroxyethyl methacrylate, hydroxypropyl acrylate, hydroxypropyl methacrylate, and the like. Particularly, 2-hydroxyethyl methacrylate is preferably used.

The $C_4$–$C_{18}$ alkyl (meth)acrylates to be used as the component (iv) of the (meth)acrylic copolymer of the present invention may include n-butyl acrylate, n-butyl methacrylate, isopropyl acrylate, isopropyl methacrylate, 2-ethylhexyl acrylate, n-hexyl methacrylate, and lauryl methacrylate. Particularly, n-butyl acrylate and 2-ethylhexyl acrylate are preferably used.

The contents of the components (i) to (iv) of the copolymer according to the present invention are as follows:

(i) $\alpha,\beta$-unsaturated carboxylic acid or its anhydride: 0.5–11.0% by weight, preferably 2.0–8.0% by weight;

(ii) Vinyl monomer: 0.1–28.0% by weight, preferably 1.0–15.0% by weight;

(iii) Hydroxy $C_2$–$C_4$ alkyl ester of (meth)acrylic acid: 1.0–5.5% by weight, preferably 1.5–4.0% by weight; and (iv) $C_4$–$C_{18}$ alkyl ester of (meth)acrylic acid: balance.

Of the above components (i) to (iv), the $\alpha,\beta$-unsaturated carboxylic acid or its anhydride and the hydroxy $C_2$–$C_4$ alkyl ester of (meth)acrylic acid are mainly used for the purpose of (1) increasing the cohesion power of the copolymer, whereby the adhesive does not remain on the skin when the tape preparations are released, (2) controlling the molecular weight of the copolymer whereby the adhesive power is controlled, and (3) increasing the solubility for ketoprofen.

When the amount used of the $\alpha,\beta$-unsaturated carboxylic acid or its anhydride or the hydroxy $C_2$–$C_4$ alkyl ester of (meth)acrylic acid is less than the above-mentioned range, the cohesion effect is weak and the solubility for ketoprofen is low. On the other hand, when said amount is more than the above-mentioned range, the cohesion property becomes too high, and thus the adhesive power is decreased, the water resistance against the diaphoresis from the skin is decreased, and the diffusibility of ketoprofen becomes unpreferably poor. Especially, when the hydroxy $C_2$–$C_4$ alkyl ester of (meth)acrylic acid is not compounded, the solubility of ketoprofen is remarkably decreased.

The vinyl monomer is used for increasing the adhesion of the copolymer. When the amount of the vinyl monomer is less than 0.1% by weight, the desired adhesion cannot be obtained, whereas when the amount exceeds 28% by weight, the resultant copolymer becomes too hard and, therefore, the adhesion is decreased and the absorbability of the drug becomes poor.

Furthermore, the $C_4$–$C_{18}$ alkyl ester of (meth)acrylic acid to be used as the component (iv) is used as a component for providing the adhesion to the copolymer. When the amount is less than, for example, 55.5% by weight, the glass transition point becomes higher so that the adhesion to the skin is decreased and the tape is released from the skin during the use thereof.

In the present invention, ketoprofen is formulated in the above-mentioned (meth)acrylic acid type copolymer and the copolymer is laminated, at a thickness of about 5 to 500 μm, preferably 10 to 200 μm on a support through which the drug is non-permeable, to form a drug supply layer.

The content formulated of ketoprofen in the drug supply layer is 5 to 35% by weight, preferably 8 to 15% by weight. If less than 5% by weight, the desired drug absorption cannot be obtained, and if over 35% by weight, the ketoprofen will be undesirably precipitated.

As the support usable in the present invention, any conventional supports can be used. Examples of such supports are flexible plastic films having a drug non-permeability, such as a soft vinyl chloride film, polyethylene film, ethylene copolymer film, polyester film, polyolefin film, polyurethane film, polyvinyl alcohol film, polypropylene film, and a cotton or nonwoven fabric.

Also, to increase the anchoring of the drug supply layer to the support or to enhance the sealability when a cotton or nonwoven fabric is used as the support, a sublayer having a thickness of 5 to 40 μm can be provided. The sublayer is not particularly limited, provided that the adhesion between the support and the drug supply layer is improved thereby, and can be exemplified by an ethylene-vinyl acetate copolymer, an acrylic or a rubber type pressure-sensitive adhesive.

As the means for forming the external dermatological agent in the present invention, the above-mentioned polymer may be obtained by solution polymerization in the presence of a solvent, the polymer solution formulated with ketoprofen therewith. The resultant formulation is coated and dried on the support, followed by uniting with a releasing layer, or the resultant formulation is coated, and dried on a releasing layer, followed by transferring the layer to the support.

The copolymerization reaction may be carried out by a known method. For example, a one-liter three-necked glass flask is set in a hot water heating system, a predetermined amount of ethyl acetate (if desired, other solvents are also added) is boiled by heating (about 80° C. in the case of ethyl acetate), and a polymerization initiator dissolved in a necessary monomer is added dropwise by a dropping funnel over a period of 3 hours. The polymerization will proceed during the addition, and the reaction completed within 4 to 5 hours after completion of the dropwise addition.

The polymerization initiator usable in the present invention may include organic peroxides such as benzoyl peroxide, azobisisobutylronitrile, lauroyl peroxide, cumene hydroperoxide, tert-butyl peroxide, ketone peroxide, and methyl ethyl ketone peroxide.

As the organic solvent, toluene, xylene, benzene, hexane, ethyl acetate, acetone, and methyl ethyl ketone may be employed.

The (meth)acrylic copolymer thus obtained has a glass transition point of −15° C. to −70° C., and preferably, a copolymer having a glass transition point of −25° C. to −40° C. is employed. Copolymers outside this range are not preferred because of an inferior adhesion thereof.

The mechanisms for absorption accelerating effects of ketoprofen according to the present invention are not clearly understood, but it is believed that the following advantages can be obtained by formulating the hydroxy $C_2$–$C_4$ alkyl ester of (meth)acrylic acid and $\alpha,\beta$-unsaturated carboxylic acid or its anhydride as the constituting monomer to the (meth)acrylic copolymer according to the present invention.

(1) The polarity of the copolymer is increased and, therefore, the drug solubility is enhanced due to the presence of the polar functional groups possessed by these monomers.

(2) The drug solubility of the copolymer according to the present invention is lower than that of, for example, copolymers containing (meth)acrylic acid alkyl ester having an ether group and vinyl alkyl ether, and therefore, the conflicting physical properties of drug solubility and diffusibility for ketoprofen, and the drug partition coefficient to the skin of ketoprofen, are excellently balanced.

EXAMPLES

The present invention will now be further illustrated in detail by, but is by no means limited to, the following Examples, wherein "parts" are all by weight unless otherwise noted.

EXAMPLE 1

A composition composed of:

| | |
|---|---|
| 2-Ethylhexyl acrylate | 86 parts |
| Vinyl acetate | 5 parts |
| Methyl acrylate | 5 parts |
| Maleic anhydride | 2 parts |
| 2-Hydroxyethyl methacrylate | 2 parts | was polymerized by using 61 parts of ethyl acetate and 1.09 parts of a polymerization initiator, azobisisobutyronitrile, in a nitrogen stream under stirring at 80° C. for 8 hours to obtain a polymer solution.

Next, 15 parts of ketoprofen based on 100 parts of the solids thereof was added to the polymer solution, while dissolving the ketoprofen in ethyl acetate. The resultant solution was applied on a peeling paper to a thickness after drying of 25 μm, followed by drying at 80° C. for 2 minutes to form a drug supply layer, which was in turn transferred onto a support of an ethylenevinyl acetate copolymer film to obtain a tape preparation of the present invention.

EXAMPLE 2

As the monomers:

| | |
|---|---|
| Lauryl methacrylate | 76 parts |
| Ethyl acrylate | 10 parts |
| Vinyl acetate | 5 parts |
| Methacrylic acid | 5 parts |
| Maleic anhydride | 1 part |
| 2-Hydroxypropyl acrylate | 3 parts | were employed, and thereafter, the same procedure as in Example 1 was followed and a tape preparation of the present invention was obtained.

EXAMPLE 3

As the monomers:

| | |
|---|---|
| Lauryl methacrylate | 71 parts |
| Methyl methacrylate | 15 parts |
| Vinyl propionate | 5 parts |
| Methacrylic acid | 4 parts |
| Maleic anhydride | 3 parts |
| 2-Hydroxypropyl acrylate | 3 parts | were employed, and thereafter, the same procedure as in Example 1 was followed and a tape preparation of the present invention was obtained.

EXAMPLE 4

As the monomers:

| | |
|---|---|
| 2-Ethylhexyl acrylate | 58 parts |
| n-Butyl acrylate | 28 parts |
| Vinyl acetate | 5 parts |
| Acrylic acid | 5 parts |
| Maleic anhydride | 2 parts |
| 2-Hydroxyethyl methacrylate | 2 parts | were employed, and thereafter, the same procedure as in Example 1 was followed and a tape preparation of the present invention was obtained.

EXAMPLE 5

As the monomers:

| | |
|---|---|
| 2-Ethylhexyl acrylate | 53 parts |
| n-Butyl acrylate | 27 parts |
| Vinyl acetate | 10 parts |
| Methacrylic acid | 3 parts |
| Maleic anhydride | 4 parts |
| 2-Hydroxypropyl methacrylate | 3 parts | were employed, and thereafter, the same procedure as in Example 1 was followed and a tape preparation of the present invention was obtained.

EXAMPLE 6

As the monomers:

| | |
|---|---|
| 2-Ethylhexyl acrylate | 42 parts |
| Ethyl acrylate | 21 parts |
| Vinyl acetate | 28 parts |
| Acrylic acid | 4 parts |
| Maleic anhydride | 2 parts |
| 2-Hydroxyethyl methacrylate | 3 parts | were employed, and thereafter, the same procedure as in Example 1 was followed and a tape preparation of the present invention was obtained.

EXAMPLE 7

As the monomers:

| | |
|---|---|
| Lauryl methacrylate | 55 parts |
| Methyl methacrylate | 27 parts |
| Vinyl propionate | 5 parts |
| Methacrylic acid | 10 parts |
| Maleic anhydride | 1 part |
| 2-Hydroxypropyl methacrylate | 2 parts | were employed, and thereafter, the same procedure as in Example 1 was followed and a tape preparation of the present invention was obtained.

EXAMPLE 8

As the monomers:

| | |
|---|---|
| 2-Ethylhexyl acrylate | 55 parts |
| n-Butyl acrylate | 28 parts |
| Vinyl propionate | 4.5 parts |
| Methacrylic acid | 5 parts |
| Maleic anhydride | 2 parts |
| 2-Hydroxyethyl methacrylate | 5.5 parts | were employed, and therafter, the same procedure as in Example 1 was followed and a tape preparation of the present invention was obtained.

EXAMPLE 9

As the monomers:

| | |
|---|---|
| 2-Ethylhexyl acrylate | 57 parts |
| Ethyl acrylate | 29 parts |
| Vinyl acetate | 0.1 part |
| Acrylic acid | 6.9 parts |
| Maleic anhydride | 2 parts |
| 2-Hydroxyethyl methacrylate | 5 parts | were employed, and thereafter, the same procedcure as in Examle 1 was followed and a tape preparation of the present invention was obtained.

EXAMPLE 10

As the monomers:

| | |
|---|---|
| Lauryl methacrylate | 57 parts |
| n-Butyl acrylate | 28 parts |
| Vinyl acetate | 10 parts |
| Maleic anhydride | 0.5 parts |
| 2-Hydroxypropyl acrylate | 4.5 parts | were employed, and thereafter, the same procedure as in Example 1 was followed and a tape preparation of the present invention was obtained.

EXAMPLE 11

As the monomers:

| | |
|---|---|
| 2-Ethylhexyl acrylate | 55 parts |
| n-Butyl acrylate | 27 parts |
| Vinyl acetate | 10 parts |
| Acrylic acid | 5 parts |
| Maleic anhydride | 2 parts |
| 2-Hydroxyethyl methacrylate | 1 part | were employed, and thereafter, the same procedure as in Example 1 was followed and a tape preparation of the present invention was obtained.

COMPARATIVE EXAMPLE 1

As the monomers:

| | |
|---|---|
| 2-Ethylhexyl acrylate | 95 parts |
| Acrylic acid | 5 parts | were employed, and thereafter, the same procedure as in Example 1 was followed and a tape preparation was obtained.

COMPARATIVE EXAMPLE 2

As the monomers:

| | |
|---|---|
| 2-Ethylhexyl acrylate | 73 parts |
| 2-Methoxyethyl acrylate | 24 parts |
| Acrylic acid | 3 parts | were employed, and thereafter, the same procedure as in Example 1 was followed and a tape preparation was obtained.

COMPARATIVE EXAMPLE 3

As the monomers:

| Lauryl methacrylate | 61 parts |
|---|---|
| Ethyl acrylate | 30 parts |
| Methacrylic acid | 5 parts |
| Maleic anhydride | 1 part |
| 2-Hydroxypropyl acrylate | 3 parts | were employed, and thereafter, the same procedure as in Example 1 was followed and a tape preparation was obtained.

COMPARATIVE EXAMPLE 4

As the monomers:

| 2-Ethylhexyl acrylate | 62 parts |
|---|---|
| n-Butyl acrylate | 31 parts |
| Vinyl acetate | 5 parts |
| 2-Hydroxyethyl methacrylate | 2 parts | were employed, and thereafter, the same procedure as in Example 1 was followed and a tape preparation was obtained.

COMPARATIVE EXAMPLE 5

As the monomers:

| 2-Ethylhexyl acrylate | 59 parts |
|---|---|
| n-Butyl acrylate | 29 parts |
| Vinyl acetate | 5 parts |
| Acrylic acid | 5 parts |
| Maleic anhydride | 2 parts | were employed, and thereafter, the same procedure as in Example 1 was followed and a tape preparation was obtained.

COMPARATIVE EXAMPLE 6

A commercially available ointment (ketoprofen content=30 mg/g of ointment) was employed instead of the tape of the present invention.

COMPARATIVE EXAMPLE 7

A commercially available poultice (ketoprofen content=30 mg/poultice) was employed instead of the tape of the present invention.

COMPARATIVE EXAMPLE 8

The same procedure as in Example 1 was followed except that indomethacin was used instead of ketoprofen, and a tape preparation was obtained.

COMPARATIVE EXAMPLE 9

The same procedure as in Example 1 was followed except that diclofenac sodium was used instead of ketoprofen, and a tape preparation was obtained.

EVALUATION EXAMPLE 1

The tape preparations prepared in Examples 1 to 11 and Comparative Examples 1 to 5 and 8 and 9 were cut into 5×5 cm squares, the commercially available poultice of Comparative Example 7 was cut into 7×7 cm squares, and with 0.33 g of the commercially available ointment of Comparative Example 6, were applied to the chests of 6 adult men.

The tape preparation or poultice preparation was peeled off 24 hours after application, and the drug remaining on the applied site was wiped off with defatted cotton containing 1 ml of distilled water. The tape preparation or poultice preparation peeled off was stirred in 200 ml of hot ethanol for 2 hours to extract the drug, cooled to room temperature, and then brought to a constant volume of 200 ml with ethanol. To 5 ml of the solution was added 5 ml of an internal standard substance (300 $\mu$g/ml of an aqueous flulubiprofen solution was used), and after bringing to a constant volume of 50 ml with ethanol, the residual drug amount was measured by high performance liquid chromatography (hereinafter abbreviated as HPLC). The defatted cotton was stirred in 200 ml of distilled water for 2 hours to extract the drug, and to 5 ml of the solution was added 5 ml of the internal standard substance. After the mixture was brought to a constant volume of 50 ml with distilled water, the remaining drug amount was measured by HPLC.

The ointment was wiped off with defatted cotton containing ethanol (10 ml of ethanol content) 24 hours after application. The wiped defatted cotton was stirred in 200 ml of hot ethanol for 2 hours to extract the drug, the extract cooled to room temperature, and then brought to a constant volume of 200 ml with ethanol. To 5 ml of the solution was added 5 ml of the above internal standard substance, and after bringing to 50 ml with ethanol, the remaining drug amount was measured by HPLC.

From the residual amount of drug measured, the drug absorption was calculated by the following formula:

$$1 - \frac{\text{Remaining amount of drug in preparation and/or applied site}}{\text{Drug amount applied}} \times 100\ (\%)$$

EVALUATION EXAMPLE 2

The tape preparations prepared in Examples 1 to 5 were cut into 7×10 cm squares, and one sheet of the commercially available poultice (10×14 cm) of Comparative Example 7 and 1 g of the commercially available ointment of Comparative Example 6 were applied to the depilated abdominal portion of a Japanese albino rabbit.

At 2, 4, 6, 10, and 24 hours after application, 1.5 ml of blood was collected from an ear vein of the rabbits and centrifuged at 3000 rpm for 10 minutes to obtain a plasma. Next, to 0.5 ml of the plasma were added 100 $\mu$l of 1N hydrochloric acid, 50 mg of sodium chloride and 50 $\mu$l of an internal standard substance (200 $\mu$g/ml aqueous flulubiprofen solution), followed by stirring. To the mixture was added 3.0 ml of ethyl acetate and the mixture was stirred and centrifuged at 3000 rpm for 3 minutes to partition the drug in the plasma to the ethyl acetate layer. This partition operation was repeated three times, and then 9 ml of the ethyl acetate layer was evaporated under a reduced pressure at 40° C. Then, the residue was dissolved in 0.5 ml of an HPLC moving phase and the drug concentration was measured by HPLC.

EVALUATION EXAMPLE 3

The tape preparation prepared in Example 4 and Comparative Examples 8 and 9 were cut into 7×10 cm squares and were placed in a polyethylene-aluminum laminate bag and all four sides of the bag were sealed.

The tape agent was stored at 40° C. and 75% R.H. for 3 months and the remaining drug amount in the tape preparation was measured in the same manner as in Evaluation Example 1.

From the residual amount of drug measured, the drug remaining rate was calculated by the following formula:

$$\frac{\text{Drug amount after 3 month storage}}{\text{Initial drug amount}} \times 100 \, (\%)$$

The results of Evaluation Examples 1 to 3 are shown in Tables 1 to 3.

TABLE 1

| Example No. | Type | Active Component | Absorption to skin (% of dose) | Excretion in urine (% of dose) |
|---|---|---|---|---|
| Ex. 1 | Tape | Ketoprofen | 41.8 ± 4.9 | 31.3 ± 4.0 |
| Ex. 2 | " | " | 39.6 ± 2.8 | 130.3 ± 2.0 |
| Ex. 3 | " | " | 38.2 ± 3.5 | 28.5 ± 2.1 |
| Ex. 4 | " | " | 47.2 ± 5.7 | 36.4 ± 4.1 |
| Ex. 5 | " | " | 36.3 ± 4.9 | 29.4 ± 4.7 |
| Ex. 6 | " | " | 29.0 ± 3.6 | 22.0 ± 3.2 |
| Ex. 7 | " | " | 33.9 ± 4.6 | 24.2 ± 2.0 |
| Ex. 8 | " | " | 34.4 ± 4.5 | 26.0 ± 4.8 |
| Ex. 9 | " | " | 30.4 ± 3.9 | 21.7 ± 3.4 |
| Ex. 10 | " | " | 27.8 ± 3.0 | 20.2 ± 2.8 |
| Ex. 11 | " | " | 24.3 ± 2.9 | 18.1 ± 2.5 |
| Com. Ex. 1 | " | " | 8.2 ± 2.7 | 4.9 ± 1.6 |
| Com. Ex. 2 | " | " | 15.1 ± 3.8 | 11.3 ± 2.8 |
| Com. Ex. 3 | " | " | 12.3 ± 2.9 | 8.2 ± 2.1 |
| Com. Ex. 4 | " | " | 7.7 ± 3.6 | 5.1 ± 1.5 |
| Com. Ex. 5 | Ointment | " | 13.2 ± 2.5 | 3.0 ± 1.7 |
| Com. Ex. 6 | Poultice | " | 15.8 ± 3.1 | 4.7 ± 1.5 |
| Com. Ex. 7 | Tape | Indomethacin | 16.1 ± 2.9 | 8.4 ± 1.9 |
| Com. Ex. 8 | " | Diclofenac sodium | 10.8 ± 2.0 | 4.8 ± 1.6 |

TABLE 2

| Example No. | Type | Active Component | Concentration (μg/ml) in plasma | | | | |
|---|---|---|---|---|---|---|---|
| | | | 2 hr | 4 hr | 6 hr | 10 hr | 24 hr |
| Ex. 1 | Tape | Ketoprofen | 0.74 ± 0.18 | 1.15 ± 0.31 | 1.14 ± 0.29 | 0.88 ± 0.28 | 0.53 ± 0.23 |
| Ex. 2 | " | " | 0.45 ± 0.15 | 0.72 ± 0.23 | 0.87 ± 0.22 | 0.71 ± 0.17 | 0.46 ± 0.13 |
| Ex. 3 | " | " | 0.41 ± 0.13 | 0.66 ± 0.19 | 0.80 ± 0.21 | 0.78 ± 0.20 | 0.37 ± 0.09 |
| Ex. 4 | " | " | 1.21 ± 0.23 | 1.58 ± 0.30 | 1.41 ± 0.23 | 1.05 ± 0.13 | 0.60 ± 0.09 |
| Ex. 5 | " | " | 0.98 ± 0.20 | 1.28 ± 0.27 | 1.27 ± 0.27 | 0.95 ± 0.21 | 0.58 ± 0.17 |
| Com. Ex. 6 | Ointment | " | 0.17 ± 0.06 | 0.29 ± 0.04 | 0.28 ± 0.04 | 0.23 ± 0.04 | 0.17 ± 0.03 |
| Com. Ex. 7 | Poultice | " | 0.40 ± 0.10 | 0.48 ± 0.12 | 0.36 ± 0.12 | 0.27 ± 0.09 | 0.15 ± 0.06 |

TABLE 3

| Example No. | Type | Active Component | Residual Amount (% of initial) |
|---|---|---|---|
| Ex. 4 | Tape | Ketoprofen | 98.7 ± 1.3 |
| Com. Ex. 8 | " | Indomethacin | 63.5 ± 5.6 |
| Com. Ex. 9 | " | Diclofenac sodium | 78.0 ± 3.2 |

As is clear from the results shown in Tables 1 and 2, the tape preparations according to the present invention (Examples 1 to 11), when compared with the tape preparations according to Comparative Examples 1 to 5 as well as the commercially available ointment (Comparative Example 6) and the commercially available poultice (Comparative Example 7), greatly enhance the percutaneous absorption of ketoprofen to bring a higher therapeutical effect compared with that of the conventional preparations.

Furthermore, as is clear from the results shown in Tables 1 and 3, when indomethacin and diclofenac sodium (both having a pharmacological activity similar to that of ketoprofen) are formulated into the (meth)acrylic copolymer used in the present invention, the percutaneous absorption of the drug and the chemical stability in the preparations are poor. Thus, it is found that ketoprofen, among the antiinflammatory agents, can be preferably used in the (meth)acrylic copolymer according to the present invention.

We claim:

1. An external dermatological composition comprising a drug supply layer carried on a support and containing 5% to 35% by weight of ketoprofen in an acrylic or methacrylic copolymer, said copolymer comprising (i) 0.5% to 11.0% by weight of an $\alpha,\beta$-unsaturated carboxylic acid or its anhydride, (ii) 0.1% to 28.0% by weight of a vinyl monomer, (iii) 1.0% to 5.5% by weight of a hydroxy $C_2$–$C_4$ alkyl ester of acrylic or methacrylic acid, and (iv) a balance of a $C_4$–$C_{18}$ alkyl ester of acrylic or methacrylic acid, and having a glass transition point of $-15°$ C. to $-70°$ C.

2. An external dermatological composition as claimed in claim 1, wherein said component (i) is at least one compound selected from the group consisting of acrylic acid, methacrylic acid, crotonic acid, itaconic acid, maleic acid, fumaric acid, and maleic anhydride.

3. An external dermatological composition as claimed in claim 1, wherein said component (ii) is at least one compound selected from the group consisting of vinyl acetate, vinyl propionate, acrylonitrile, styrene, vinyl versatate, and vinyl chloride.

4. An external dermatological composition as claimed in claim 1, wherein said component (iii) is at least one compound selected from the group consisting of 2-hydroxyethyl acrylate, 2-hydroxyethyl methacrylate, hydroxypropyl acrylate, and hydroxypropyl methacrylate.

5. An external dermatological composition as claimed in claim 1, wherein said component (iv) is at least one compound selected from the group consisting of n-butyl acrylate, n-butyl methacrylate, isopropyl acrylate, isopropyl methacrylate, 2-ethylhexyl acrylate, n-hexyl methacrylate, and lauryl methacrylate.

6. An external dermatological composition as claimed in claim 1, wherein said copolymer comprises (i) 2.0% to 8.0% by weight of an α,β-unsaturated carboxylic acid or its anhydride, (ii) 1.0% to 15.0% by weight of a vinyl monomer, (iii) 1.5% to 4.0% by weight of a hydroxy $C_2$–$C_4$ alkyl ester of acrylic or methacrylic acid, and (iv) a balance of a $C_4$–$C_{18}$ alkyl ester of acrylic or methacrylic acid.

7. An external dermatological composition as claimed in claim 1, wherein said copolymer has a glass transition point of −25° C. to −40° C.

8. An external dermatological composition as claimed in claim 1, wherein said support is a flexible plastic film having drug non-permeability and having a thickness of 5 to 40 μm.

9. An external dermatological composition as claimed in claim 1, wherein said composition is in the form of a drug supply layer having a thickness 5 to 500 μm on the support.

* * * * *